(12) United States Patent
DeSimone et al.

(10) Patent No.: US 6,448,259 B1
(45) Date of Patent: *Sep. 10, 2002

(54) SUBSTITUTED CYCLOALKYL-4-OXONICOTINIC CARBOXAMIDES; GABA BRAIN RECEPTOR LIGANDS

(75) Inventors: Robert W. DeSimone, Durham; Daniel L. Rosewater, Branford, both of CT (US)

(73) Assignee: Neurogen Corporation, Branford, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/565,531

(22) Filed: May 5, 2000

Related U.S. Application Data

(63) Continuation of application No. 09/259,244, filed on Feb. 26, 1999, now Pat. No. 6,194,427.
(60) Provisional application No. 60/076,022, filed on Feb. 26, 1998.

(51) Int. Cl.⁷ ................. A61K 31/435; A61K 31/4709; C07D 221/04; C07D 215/233; A61P 25/00
(52) U.S. Cl. .................. 514/299; 514/256; 514/275; 514/310; 514/312; 544/331; 544/328; 546/156; 546/183; 546/143; 546/112
(58) Field of Search ................. 546/156, 183, 546/143, 112; 544/328, 331; 514/299, 275, 256, 310, 312

(56) References Cited

U.S. PATENT DOCUMENTS

| | | | | |
|---|---|---|---|---|
| 4,943,314 A | * | 7/1990 | Goto | 71/94 |
| 6,177,569 B1 | | 1/2001 | Rachwal et al. | |

FOREIGN PATENT DOCUMENTS

| | | |
|---|---|---|
| DE | 2 407 744 | 2/1974 |
| EP | 0 067 772 A1 | 12/1982 |
| EP | 0 070 767 A1 | 1/1983 |
| EP | 0 180 318 A1 | 5/1986 |
| JP | 62-167709 A2 * | 7/1987 |
| JP | 62-167709 | 7/1987 |
| JP | 62-249973 | 10/1987 |
| JP | 62-249973 A2 * | 10/1987 |
| WO | WO 97/34870 | 9/1997 |
| WO | WO 98/02420 | 1/1998 |

OTHER PUBLICATIONS

Roberts & Frankel, J. Biol. Chem. 187: 55–63, 1950.
Udenfriend, J. Biol. Chem. 187: 65–69, 1950.
Tallman and Gallager, Ann. Rev. Neuroscience 8: 21–44, 1985.
Barnard et al., Pharmacological Reviews vol. 50 No. 2, pp. 291–313, 1998.
Maryanoff et al., Journal of Medicinal Chemistry vol. 38, pp. 16–20, 1995.
Maryanoff et al., Bioorganic & Medicinal Chemistry Letters vol. 6, No. 3, pp. 333–338, 1996.
Kilbourn et al., Journal of Organic Chemistry vol. 37, No. 8, pp. 1145–1148, 1972.

* cited by examiner

Primary Examiner—Evelyn Mei Huang
(74) Attorney, Agent, or Firm—McDonnell Boehnen Hulbert & Berghoff

(57) ABSTRACT

Disclosed are compounds of the Formula:

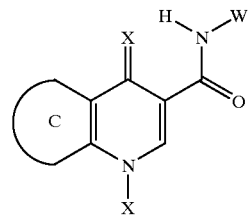

or the pharmaceutically acceptable non-toxic salts thereof wherein:

the C ring is a(n) (un)substituted carbocycle;

X is hydrogen, hydroxyl or lower alkyl; and W is (un)substituted alkyl, aryl, arylalkyl, or heteroaryl, which compounds are highly selective agonists, antagonists or inverse agonists for GABAa brain receptors or prodrugs of agonists, antagonists or inverse agonists for GABAa brain receptors. These compounds are useful in the diagnosis and treatment of anxiety, sleep and seizure disorders, overdose with benzodiazepine drugs and for enhancement of memory.

19 Claims, No Drawings

US 6,448,259 B1

SUBSTITUTED CYCLOALKYL-4-OXONICOTINIC CARBOXAMIDES; GABA BRAIN RECEPTOR LIGANDS

This application is the continuation of Ser. No. 09/259,244, filed Feb. 26, 1989, now U.S. Pat. No. 6,194,427, which claims benefit of Ser. No. 60/026,022, filed Feb. 26, 1998.

BACKGROUND OF THE INVENTION

1. Field of the Invention

This invention relates to certain substituted cycloalkyl-4-oxonicotinic carboxamides. In particular it relates to such compounds that selectively bind to GABAa receptors. This invention also relates to pharmaceutical compositions comprising such compounds. It further relates to the use of such compounds in treating anxiety, sleep and seizure disorders, and overdoses of benzodiazepine-type drugs, and enhancing alertness.

2. Description of the Related Art

γ-Aminobutyric acid (GABA) is regarded as one of the major inhibitory amino acid transmitters in the mammalian brain. Over 40 years have elapsed since its presence in the brain was demonstrated (Roberts & Frankel, J. Biol. Chem 187: 55–63, 1950; Udenfriend, J. Biol. Chem. 187: 65–69, 1950). Since that time, an enormous amount of effort has been devoted to implicating GABA in the etiology of seizure disorders, sleep, anxiety and cognition (Tallman and Gallager, Ann. Rev. Neuroscience 8: 21–44, 1985). Widely, although unequally, distributed through the mammalian brain, GABA is said to be a transmitter at approximately 30% of the synapses in the brain. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Recent investigations have indicated that the complex of proteins associated with postsynaptic GABA responses is a major site of action for a number of structurally unrelated compounds capable of modifying postsynaptic responses to GABA. Drugs that interact at the GABAa receptor can possess a spectrum of pharmacological activities depending on their abilities to modify the actions of GABA.

1,4-Benzodiazepines, such as diazepam, flurazepam, and triazolam continue to be among the most widely used as anxiolytics, sedative-hypnotics, muscle relaxants, and anticonvulsants. A number of these compounds are extremely potent drugs; such potency indicates a site of action with a high affinity and specificity for individual receptors. Early electrophysiological studies indicated that a major action of benzodiazepines was enhancement of GABAergic inhibition. Presently, those compounds possessing activity which enhance the effect of GABA are called agonists, those compounds which decrease the effect of GABA are called inverse agonists, and those compounds which block the effect of GABA are called antagonists.

The GABAa receptor subunits have been cloned from bovine and human cDNA libraries (Schoenfield et al., 1988; Duman et al., 1989). A number of distinct cDNAs were identified as subunits of the GABAa receptor complex by cloning and expression. These are categorized into α, β, γ, δ, ε, and provide a molecular basis for the GABAa receptor heterogeneity and distinctive regional pharmacology (Shivvers et al., 1980; Levitan et al., 1989). The γ subunit appears to enable drugs like benzodiazepines to modify the GABA responses (Pritchett et al., 1989). The presence of low Hill coefficients in the binding of ligands to the GABAa receptor indicates unique profiles of subtype specific pharmacological action.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified system, in turn, may be associated with the expression of a behavior. Depending on the mode of interaction, these compounds are capable of producing a spectrum of activities (either sedative, anxiolytic, and anticonvulsant, or wakefulness, seizures, and anxiety).

SUMMARY OF THE INVENTION

This invention provides novel compounds of Formula I which interact with a GABAa binding site, the benzodiazepine receptor.

The invention provides pharmaceutical compositions comprising compounds of Formula I. The invention also provides compounds useful in the diagnosis and treatment of anxiety, sleep, and seizure disorders, overdose with benzodiazepine drugs and for enhancement of memory. Accordingly, a broad embodiment of the invention is directed to compounds of Formula I:

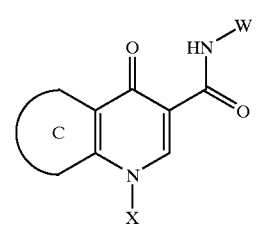

wherein:
   the C ring represents a carbocyclic group having from 5–7 members, where any member of the carbocyclic group is optionally mono-, di-, or trisubstituted with lower alkyl, $C_1$–$C_6$ alkoxy, hydroxy, halogen, amino, mono- or di ($C_1$–$C_6$)alkylamino, or trifluoromethyl;
   X is hydrogen, hydroxy, or lower alkyl; and
   W is lower alkyl optionally substituted with halogen, hydroxy, lower alkoxy, amino, or mono- or dialkyl amino where each alkyl portion is lower alkyl; or
   W is aryl, arylalkyl, or heteroaryl, where each aryl is optionally substituted with one or two groups independently selected from halogen, trifluoromethyl, cyano, hydroxy, lower alkyl, lower alkoxy, amino, mono- or dialkylamino where each alkyl portion is lower alkyl, mono- or dialkylaminoalkyl where each alkyl portion is lower alkyl, or $NR_1COR_2$, $COR_2$, $CONR_1R_2$ or $CO_2R_2$ where $R_1$ and $R_2$ are the same or different and represent hydrogen or lower alkyl, or $NR_1R_2$ form a 5, 6, or 7-membered ring having one ring member optionally replaced with oxygen or nitrogen.

These compounds are highly selective agonists, antagonists or inverse agonists for GABAa brain receptors or prodrugs of agonists, antagonists or inverse agonists for GABAa brain receptors. These compounds are useful in the diagnosis and treatment of anxiety, sleep and seizure disorders, overdose with benzodiazepine drugs and for enhancement of memory.

DETAILED DESCRIPTION OF THE INVENTION

The novel compounds encompassed by the instant invention can be described by general Formula I set forth above or the pharmaceutically acceptable non-toxic salts thereof.

In addition, the present invention also encompasses compounds of Formula II:

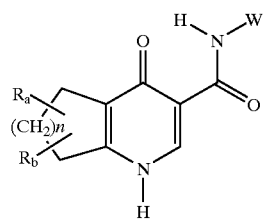

wherein:
- $R_a$ is hydrogen, lower alkyl, $C_1$–$C_6$ alkoxy, hydroxy, halogen, amino, mono- or di($C_1$–$C_6$)alkylamino, or trifluoromethyl;
- $R_b$ is hydrogen, lower alkyl, $C_1$–$C_6$ alkoxy, hydroxy, halogen, amino, mono- or di($C_1$–$C_6$)alkylamino, or trifluoromethyl;
- n is an integer from 1–3; and
- X is hydrogen or $C_1$–$C_6$ alkyl;
- W is lower alkyl optionally substituted with halogen, hydroxy, lower alkoxy, amino, or mono- or dialkyl amino where each alkyl portion is lower alkyl; or
- W is aryl, arylalkyl, or heteroaryl, where each aryl is optionally substituted with one or two groups independently selected from halogen, trifluoromethyl, cyano, hydroxy, lower alkyl, lower alkoxy, amino, mono or dialkylamino where each alkyl portion is lower alkyl, alkylaminoalkyl, preferably methylaminoalkyl, where each alkyl portion is lower alkyl, or $NR_1COR_2$, $COR_2$, $CONR_1R_2$ or $CO_2R_2$ where $R_1$ and $R_2$ are the same or different and represent hydrogen or lower alkyl.

Preferred compounds of Formula II are where W is an optionally substituted aryl, arylalkyl, or heteroaryl. Other preferred compounds of II are those where only one of $R_a$ and $R_b$ may be non-hydrogen substituents; preferably the $R_a$ and $R_b$ groups are independently $C_1$–$C_2$ alkyl, or more preferably, hydrogen. Still other preferred compounds of Formula II are those where X is $C_1$–$C_6$ alkyl or hydrogen, preferably hydrogen.

More preferred compounds of Formula II are where W is phenyl, benzyl, thienyl, thiazolyl, or pyridyl each of which is optionally substituted with one or two groups independently selected from halogen, trifluoromethyl, cyano, hydroxy, lower alkyl, lower alkoxy, amino, mono or dialkylamino where each alkyl portion is lower alkyl, methylaminoalkyl where each alkyl portion is lower alkyl, or $NR_1COR_2$, $COR_2$, $CONR_1R_2$ or $CO_2R_2$ where $R_1$ and $R_2$ are the same or different and represent hydrogen or lower alkyl.

Even more preferred compounds of Formula II are W is phenyl, benzyl, thienyl, thiazolyl, or pyridinyl each of which is optionally substituted with one or two groups independently selected from halogen, hydroxy, lower alkyl, or lower alkoxy.

Other more preferred compounds of Formula II are those where the W group is mono- or disubstituted with a halogen selected from chloro, bromo, or fluoro, amino, mono- or di($C_1$–$C_2$)alkylamino($C_1$–$C_2$)alkyl, $C_1$–$C_3$ alkoxy, $C_1$–$C_3$ alkyl, or hydroxy.

In addition, the present invention encompasses compounds of the Formula III:

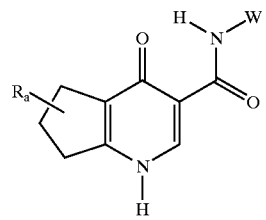

wherein:
- $R_a$ is hydrogen, lower alkyl, $C_1$–$C_6$ alkoxy, hydroxy, halogen, amino, mono- or di($C_1$–$C_6$)alkylamino, or trifluoromethyl;
- W is lower alkyl optionally substituted with halogen, hydroxy, lower alkoxy, amino, or mono- or dialkyl amino where each alkyl portion is lower alkyl; or
- W is aryl, arylalkyl, or heteroaryl, where each aryl is optionally substituted with one or two groups independently selected from halogen, trifluoromethyl, cyano, hydroxy, lower alkyl, lower alkoxy, amino, mono or dialkylamino where each alkyl portion is lower alkyl, methylaminoalkyl where each alkyl portion is lower alkyl, or $NR_1COR_2$, $COR_2$, $CONR_1R_2$ or $CO_2R_2$ where $R_1$ and $R_2$ are the same or different and represent hydrogen or lower alkyl.

Preferred compounds of Formula III are where W is an optionally substituted aryl, arylalkyl, or heteroaryl.

More preferred compounds of Formula III are where W is phenyl, benzyl, thiophene, thiazolyl, pyridinyl, or piperonyl each of which is optionally substituted with one or two groups independently selected from halogen, trifluoromethyl, cyano, hydroxy, lower alkyl, lower alkoxy, amino, mono- or dialkylamino where each alkyl portion is lower alkyl, methylaminoalkyl where each alkyl portion is lower alkyl, or $NR_1COR_2$, $COR_2$, $CONR_1R_2$ or $CO_2R_2$ where $R_1$ and $R_2$ are the same or different and represent hydrogen or lower alkyl.

Even more preferred compounds of Formula III are where W is phenyl, benzyl, thiophene, thiazolyl, or pyridinyl each of which is optionally substituted with one or two groups independently selected from $C_1$–$C_3$ alkyl, more preferably methyl, fluorine, or methoxy.

In addition, the present invention encompasses compounds of the Formula IV.

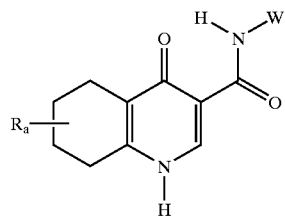

wherein:
- $R_a$ is hydrogen, lower alkyl, $C_1$–$C_6$ alkoxy, hydroxy, halogen, amino, mono- or di($C_1$–$C_6$)alkylamino, or trifluoromethyl;
- W is lower alkyl optionally substituted with halogen, hydroxy, lower alkoxy, amino, or mono- or dialkyl amino where each alkyl portion is lower alkyl; or W is aryl, arylalkyl, or heteroaryl, where each aryl is optionally substituted with one or two groups independently selected from halogen, trifluoromethyl, cyano, hydroxy, lower alkyl, lower alkoxy, amino, mono or dialkylamino where each alkyl portion is lower alkyl, methylaminoalkyl where each alkyl portion is lower alkyl, or $NR_1COR_2$, $COR_2$, $CONR_1R_2$ or $CO_2R_2$ where $R_1$ and $R_2$ are the same or different and represent hydrogen or lower alkyl.

Preferred compounds of Formula IV are where W is an optionally substituted aryl, arylalkyl, or heteroaryl.

More preferred compounds of Formula IV are where W is phenyl, benzyl, thiophene, thiazolyl, pyridinyl, or piperonyl each of which is optionally substituted with one or two groups independently selected from halogen, trifluoromethyl, cyano, hydroxy, lower alkyl, lower alkoxy, amino, mono- or dialkylamino where each alkyl portion is lower alkyl, methyl or ethyl aminoalkyl where each alkyl portion is lower alkyl, or $NR_1COR_2$, $COR_2$, $CONR_1R_2$ or $CO_2R_2$ where $R_1$ and $R_2$ are the same or different and represent hydrogen or lower alkyl.

Even more preferred compounds of Formula IV are where W is phenyl, benzyl, thiophene, thiazolyl, or pyridinyl each of which is optionally substituted with one or two groups independently selected from methyl, fluorine, hydroxy, or methoxy or $C_1$–$C_3$ alkyl, preferably methyl.

In addition, the present invention encompasses compounds of the Formula V.

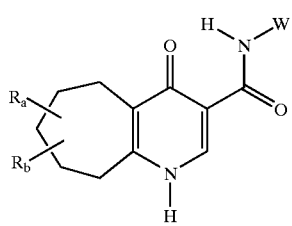

V wherein:

$R_a$ is hydrogen, lower alkyl, $C_1$–$C_6$ alkoxy, hydroxy, halogen, amino, mono- or di($C_1$–$C_6$)alkylamino, or trifluoromethyl;

$R_b$ is lower alkyl, $C_1$–$C_6$ alkoxy, hydroxy, halogen, amino, mono- or di($C_1$–$C_6$)alkylamino, or trifluoromethyl;

W is lower alkyl optionally substituted with halogen, hydroxy, lower alkoxy, amino, or mono- or dialkyl amino where each alkyl portion is lower alkyl; or W is aryl, arylalkyl, or heteroaryl, where each aryl is optionally substituted with one or two groups independently selected from halogen, trifluoromethyl, cyano, hydroxy, lower alkyl, lower alkoxy, amino, mono or dialkylamino where each alkyl portion is lower alkyl, methylaminoalkyl where each alkyl portion is lower alkyl, or $NR_1COR_2$, $COR_2$, $CONR_1R_2$ or $CO_2R_2$ where $R_1$ and $R_2$ are the same or different and represent hydrogen or lower alkyl.

Preferred compounds of Formula V are where W is an optionally substituted aryl, arylalkyl, or heteroaryl.

More preferred compounds of Formula V are where W is phenyl, benzyl, thiazolyl, pyridinyl, or piperonyl each of which is optionally substituted with one or two groups independently selected from halogen, trifluoromethyl, cyano, hydroxy, lower alkyl, lower alkoxy, amino, mono- or dialkylamino where each alkyl portion is lower alkyl, methylaminoalkyl where each alkyl portion is lower alkyl, or $NR_1COR_2$, $COR_2$, $CONR_1R_2$ or $CO_2R_2$ where $R_1$ and $R_2$ are the same or different and represent hydrogen or lower alkyl.

Even more preferred compounds of Formula IV are where W is phenyl, benzyl, or thiazolyl each of which is optionally substituted with one or two groups independently selected from chloro, fluoro, ethoxy or methoxy.

Preferred compounds of the invention are encompassed by the following formulae:

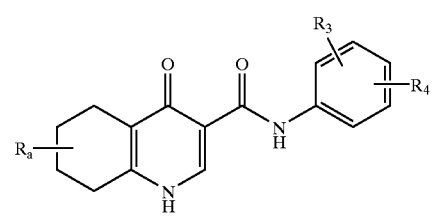

VI wherein:

$R_a$ is hydrogen, lower alkyl, $C_1$–$C_6$ alkoxy, hydroxy, halogen, amino, mono- or di($C_1$–$C_6$)alkylamino, or trifluoromethyl;

$R_3$ and $R_4$ are the same or different and represent hydrogen, halogen, hydroxy, lower alkyl, lower alkoxy, amino, mono- or dialkylamino where each alkyl portion is lower alkyl, methylaminoalkyl where each alkyl portion is lower alkyl, or $NR_1COR_2$, $COR_2$, $CONR_1R_2$ or $CO_2R_2$ where $R_1$ and $R_2$ are the same or different and represent hydrogen or lower alkyl.

More preferred compounds of Formula VI are where $R_a$ is hydrogen, methyl or ethyl, $R_3$ is hydrogen or halogen and $R_4$ is halogen, hydroxy, or lower alkoxy.

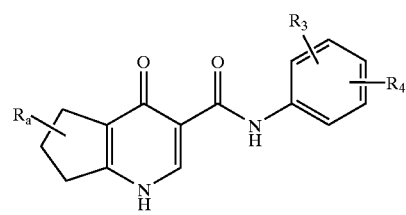

VII wherein:

$R_a$ is hydrogen, lower alkyl, $C_1$–$C_6$ alkoxy, hydroxy, halogen, amino, mono- or di($C_1$–$C_6$)alkylamino, or trifluoromethyl;

$R_3$ and $R_4$ are the same or different and represent hydrogen, halogen, hydroxy, lower alkyl, lower alkoxy, amino, mono- or dialkylamino where each alkyl portion is lower alkyl, or methylaminoalkyl where each alkyl portion is lower alkyl, or $NR_1COR_2$, $COR_2$, $CONR_1R_2$ or $CO_2R_2$ where $R_1$ and $R_2$ are the same or different and represent hydrogen or lower alkyl.

More preferred compounds of Formula VII are where $R_3$ is hydrogen or halogen, $R_a$ is hydrogen, methyl or ethyl, and $R_4$ is halogen, hydroxy, or lower alkoxy.

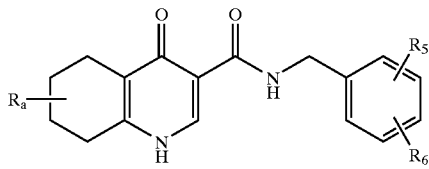

VIII wherein:
R$_a$ is hydrogen, lower alkyl, C$_1$–C$_6$ alkoxy, hydroxy, halogen, amino, mono- or di(C$_1$–C$_6$)alkylamino, or trifluoromethyl;

R$_5$ and R$_6$ are the same or different and represent hydrogen, halogen, hydroxy, lower alkyl, lower alkoxy, amino, mono- or dialkylamino where each alkyl portion is lower alkyl, methylaminoalkyl where each alkyl portion is lower alkyl, or NR$_1$COR$_2$, COR$_2$, CONR$_1$R$_2$ or CO$_2$R$_2$ where R$_1$ and R$_2$ are the same or different and represent hydrogen or lower alkyl.

More preferred compounds of Formula VIII are where R$_5$ is hydrogen or halogen and R$_6$ is halogen, hydroxy, or lower alkoxy.

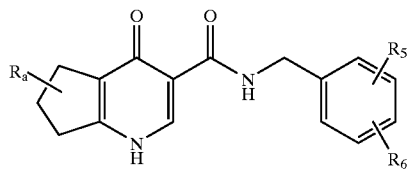

IX wherein:
R$_a$ is hydrogen, lower alkyl, C$_1$–C$_6$ alkoxy, hydroxy, halogen, amino, mono- or di(C$_1$–C$_6$)alkylamino, or trifluoromethyl;

R$_5$ and R$_6$ are the same or different and represent hydrogen, halogen, hydroxy, lower alkyl, lower alkoxy, amino, mono- or dialkylamino where each alkyl portion is lower alkyl, methylaminoalkyl where each alkyl portion is lower alkyl, or NR$_1$COR$_2$, COR$_2$, CONR$_1$R$_2$ or CO$_2$R$_2$ where R$_1$ and R$_2$ are the same or different and represent hydrogen or lower alkyl.

More preferred compounds of Formula IX are where R$_5$ is hydrogen or halogen and R$_6$ is halogen, hydroxy, or lower alkoxy.

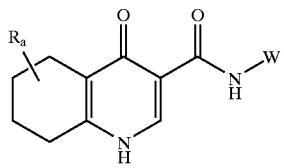

X wherein:
R$_a$ is hydrogen, lower alkyl, C$_1$–C$_6$ alkoxy, hydroxy, halogen, amino, mono- or di(C$_1$–C$_6$)alkylamino, or trifluoromethyl;

W is 2-, 3-, or 4-pyridyl, 2- or 3-thienyl, or 2-thiazolyl, each of which may be independently substituted with halogen, hydroxyl, lower alkyl, lower alkoxy, amino, methylaminoalkyl where each alkyl portion is lower alkyl, or NR$_1$COR$_2$, COR$_2$, CONR$_1$R$_2$ or CO$_2$R$_2$ where R$_1$ and R$_2$ are the same or different and represent hydrogen or lower alkyl.

More preferred compounds of Formula X are where W is 2-, 3-, or 4-pyridyl, 2- or 3-thienyl, or 2-thiazolyl, each of which may be independently substituted with halogen, lower alkyl, or lower alkoxy.

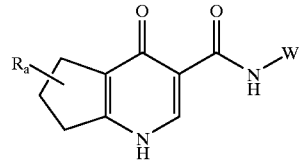

XI wherein:
R$_a$ is hydrogen, lower alkyl, C$_1$–C$_6$ alkoxy, hydroxy, halogen, amino, mono- or di(C$_1$–C$_6$)alkylamino, or trifluoromethyl;

W is 2-, 3-, or 4-pyridyl, 2- or 3-thienyl, or 2-thiazolyl, each of which may be independently substituted with halogen, hydroxyl, lower alkyl, lower alkoxy, amino, methylaminoalkyl where each alkyl portion is lower alkyl, or NR1COR$_2$, COR$_2$, CONR$_1$R$_2$ or CO$_2$R$_2$ where R$_1$ and R$_2$ are the same or different and represent hydrogen or lower alkyl.

More preferred compounds of Formula X are where W is 2-, 3-, or 4-pyridyl, 2- or 3-thienyl, or 2-thiazolyl, each of which may be independently substituted with halogen, lower alkyl, or lower alkoxy.

By "alkyl" and "lower alkyl" in the present invention is meant straight or branched chain alkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "alkoxy" and "lower alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By the term "halogen" in the present invention is meant fluorine, bromine, chlorine, and iodine.

By heteroaryl is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, napthyridinyl, benzimidazolyl, benzoxazolyl. Preferred heteroaryl groups are optionally substituted pyridyl, pyrimidinyl, naphthyridinyl, benzimidazolyl, and imidazolyl groups.

By aryl is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy. Preferred aryl groups are optionally substituted phenyl and naphthyl groups.

Representative compounds of the invention are shown below in Table 1.

TABLE 1
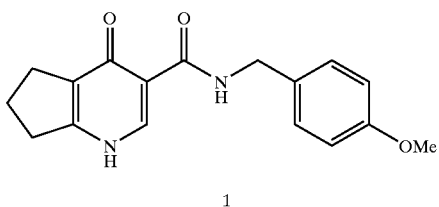
1
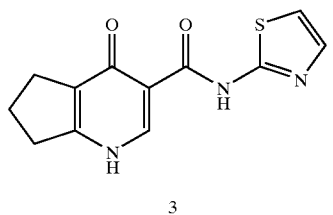
3
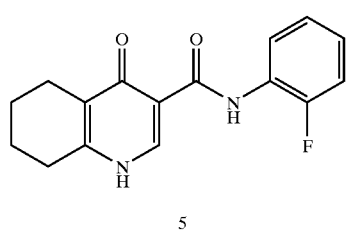
5
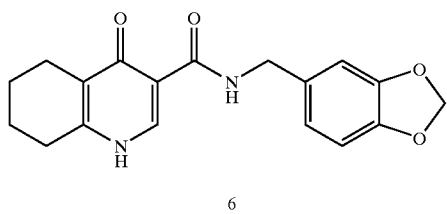
6
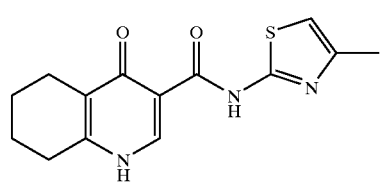
11
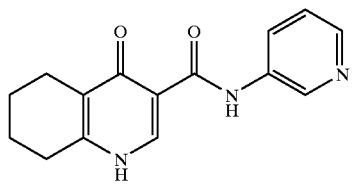
13
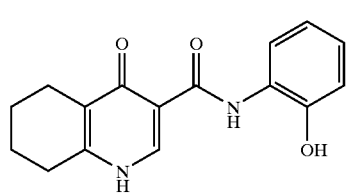
14
TABLE 1-continued
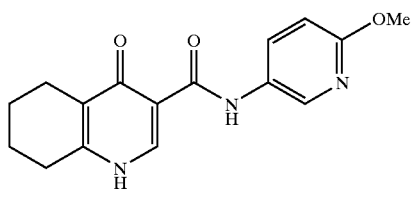
15
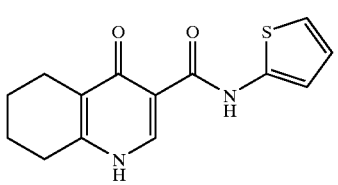
20
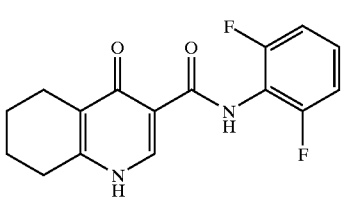
23
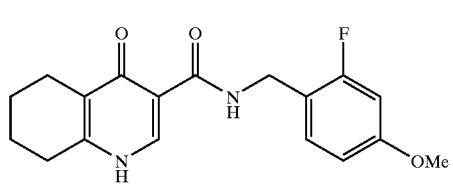
27
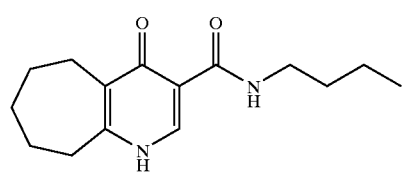
39
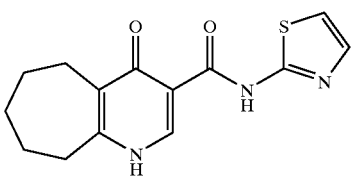
40
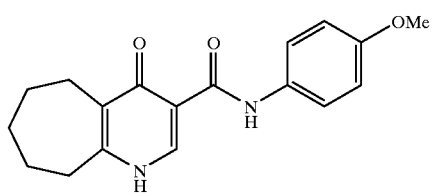
41

TABLE 1-continued

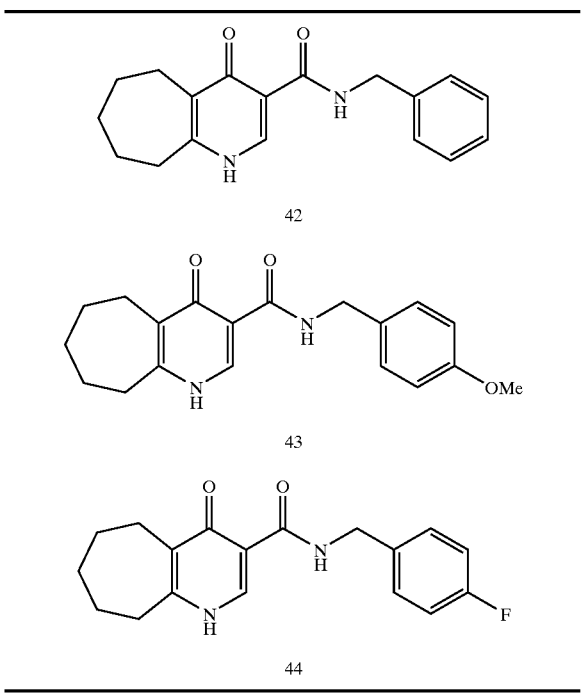

Representative compounds of the present invention, which are encompassed by Formula I, include, but are not limited to the compounds in Table 1 and their pharmaceutically acceptable salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)$_n$—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

The compounds of Formula I and their salts are suitable for the diagnosis and treatment of anxiety, Down Syndrome, sleep, cognitive and seizure disorders, and overdose with benzodiazepine drugs and for enhancement of alertness, both in human and non-human animals and domestic pets, especially dogs and cats and farm animals such as sheep, swine and cattle.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It will be convenient to formulate these animal feed and drinking water compositions with a mullet-dose of the drug so that the animal takes in an appropriate quantity of the composition along with its diet. It will also be convenient to present the composition as a premix for addition to the feed or drinking water.

An illustration of the preparation of compounds of the present invention is given in Scheme I. The appropriate pyridin-4-one-3-carboxylic acid is prepared essentially according to the procedures described in *J. Het. Chem.* 1975, 1245.

Scheme I

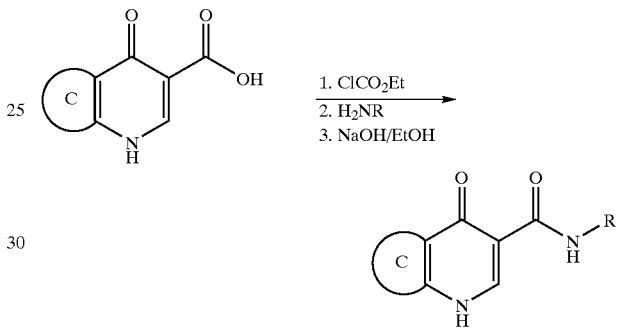

where the c-ring, X, and W carry the definitions given above for Formula I.

Those having skill in the art will recognize that the starting materials may be varied and additional steps employed to produce compounds encompassed by the present invention, as demonstrated by the following examples.

As shown in Scheme I, the appropriate pyridin-4-one-3-carboxylic acid is treated with an acid chloride, such as, for example, ethyl chloroformate, in the presence of a base like triethylamine. The resulting mixed anhydride is subsequently treated with an amine to afford the desired amide.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

Representative examples of methods for preparing intermediates of the invention are set forth below.

EXAMPLE 1

N-(4-Methoxybenzyl)-4,5,6,7-tetrahydro-1H-cyclopenta[b]pyridin-4-one-3-carboxamide A quantity of 100 mg (0.61 mmole, 1.0 eq) of 4,5,6,7-tetrahydro-1H-cyclopenta[b]pyridin-4-one-3-carboxylic acid is dissolved in 5 mL THF and 1 mL DMF and treated at 0° C. with 0.18 mL (1.2 mmole, 2.2 eq) TEA followed by 0.12 mL (1.2 mmole, 2.2 eq) of ethyl chloroformate. The resulting solution is stirred for 30 min. at which time 0.17 mL (1.2 mmole, 2.2 eq) of 4-methoxybenzylamine is added. The solution is allowed to warm to room temperature for 1 hr before the addition of 20 mL of $H_2O$, the THF is removed under reduced pressure, and the resulting solid is filtered and washed with $H_2O$ and then $Et_2O$. The resulting solid is slurried in 1 mL EtOH and 5 mL 10% NaOH, warmed to 90° C. for 10 min., cooled to 0° C., and pH adjusted to 9.0 with 3N $HC_1$. The resulting solid is filtered, washed with $H_2O$, $Et_2O$, and purified by chromatography (silica gel, 10% $CH_3OH/CH_2Cl_2$), to yield 89 mg of N-(4-Methoxybenzyl)-4,5,6,7-tetrahydro-1H-cyclopenta[b]pyridin-4-one-3-carboxamide (compound 1), mp 240–241° C.

EXAMPLE 2

N-(2-Fluorophenyl)-1,4,5,6,7,8-hexahydroquinolin-4-one-3-carboxanide

A quantity of 100 mg (0.52 mmole, 1.0 eq) of 1,4,5,6,7,8-hexahydroquinolin-4-one-3-carboxylic acid is dissolved in 5 mL THF and 1 mL DMF and treated at 0° C. with 0.16 mL (1.14 mmole, 2.2 eq) TEA followed by 0.11 ml (1.14 mmole, 2.2 eq) of ethyl chloroformate. The resulting solution is stirred for 30 min at which time, 0.15 mL (1.14 mmole, 2.2 eq) of 4-methoxybenzyl amine is added. The solution is allowed to warm to room temperature for 1 hr before the addition 20 mL $H_2O$, the THF is removed under reduced pressure, and the resulting solid is filtered and washed with $H_2O$, then $Et_2O$, and purified by chromatography (silica gel, 10% $CH_3OH/CH_2Cl_2$),to yield 102 mg of N-(2-Fluorophenyl)-1,4,5,6,7,8-hexahydroquinolin-4-one-3-carboxamide (compound 5), mp 241–244° C.

EXAMPLE 3

The following compounds are prepared essentially according to the procedures setforth in Examples 1 and 2.

(a) N-(4-methoxybenzyl)-1,4,5,6,7,8-hexahydroquinolin-4-one-3-carboxamide; mp=241–244° C. (Compound 2).

(b) N-(2-thiazolyl)-4,5,6,7-tetrahydro-1H-cyclopenta[b]pyridin-4-one-3-carboxamide; mp=305° (dec.) (Compound 3).

(c) N-(phenyl)-4,5,6,7-tetrahydro-1H-cyclopenta[b]pyridin-4-one-3-carboxamide; mp=295–296° C. (Compound 4).

(d) N-(piperonyl)-1,4,5,6,7,8-hexahydroquinolin-4-one-3-carboxamide; mp=263–265° C. (Compound 6).

(e) N-(3-fluorophenyl)-1,4,5,6,7,8-hexahydroquinolin-4-one-3-carboxamide; mp=319–320° C. (Compound 7).

(f) N-(phenyl)-1,4,5,6,7,8-hexahydroquinolin-4-one-3-carboxamide; mp=299–300° C. (Compound 8).

(g) N-(2-thiazolyl)-1,4,5,6,7,8-hexahydroquinolin-4-one-3-carboxamide; mp=260° (dec.) (Compound 9).

(h) N-(4-methoxyphenyl)-1,4,5,6,7,8-hexahydroquinolin-4-one-3-carboxamide; mp=287–290° C. (Compound 10).

(i) N-(4-methyl-2-thiazolyl)-1,4,5,6,7,8-hexahydroquinolin-4-one-3-carboxamide; mp=350–352° C. (Compound 11).

(j) N-(4-fluorophenyl)-1,4,5,6,7,8-hexahydroquinolin-4-one-3-carboxamide; mp=324–326° C. (Compound 12).

(k) N-(3-pyridyl)-1,4,5,6,7,8-hexahydroquinolin-4-one-3-carboxamide; mp=308° (dec.) (Compound 13).

(l) N-(2-hydroxyphenyl)-1,4,5,6,7,8-hexahydroquinolin-4-one-3-carboxamide; mp=2950 (dec.) (Compound 14).

(m) N-(4-methoxypyrid-3-yl)-1,4,5,6,7,8-hexahydroquinolin-4-one-3-carboxamide; mp=292° (dec.) (Compound 15).

(n) N-(3-methoxyphenyl)-1,4,5,6,7,8-hexahydroquinolin-4-one-3-carboxamide; mp=275–280° C. (Compound 16).

(o) N-(4-methoxypyrid-2-yl)-1,4,5,6,7,8-hexahydroquinolin-4-one-3-carboxamide; mp=312° (dec.) (Compound 17).

(p) N-(3-hydroxybenzyl)-1,4,5,6,7,8-hexahydroquinolin-4-one-3-carboxamide; mp=133–136° C. (Compound 18).

(q) N-(benzyl)-1,4,5,6,7,8-hexahydroquinolin-4-one-3-carboxamide; mp=257–259° C. (Compound 19).

(r) N-(2-thienyl)-1,4,5,6,7,8-hexahydroquinolin-4-one-3-carboxamide; mp=306° (dec.) (Compound 20).

(s) N-(2-chlorophenyl)-1,4,5,6,7,8-hexahydroquinolin-4-one-3-carboxamide; mp=339–341° C. (Compound 21).

(t) N-(3-thienyl)-1,4,5,6,7,8-hexahydroquinolin-4-one-3-carboxamide; mp=321–324° C. (Compound 22).

(u) N-(2,6-difluorophenyl)-1,4,5,6,7,8-hexahydroquinolin-4-one-3-carboxamide; mp=278–280° C. (Compound 23).

(v) N-(2-methoxybenzyl)-1,4,5,6,7,8-hexahydroquinolin-4-one-3-carboxamide; mp=217–219° C. (Compound 24).

(w) N-(3-methoxybenzyl)-1,4,5,6,7,8-hexahydroquinolin-4-one-3-carboxamide; mp=210–212° C. (Compound 25).

(x) N-(2-fluorobenzyl)-1,4,5,6,7,8-hexahydroquinolin-4-one-3-carboxamide; mp=206–208° C. (Compound 26).

(y) N-(2-fluoro-4-methoxyphenyl)-1,4,5,6,7,8-hexahydroquinolin-4-one-3-carboxamide; mp=257–259° C. (Compound 27).

(z) N-(2-pyridyl)-4,5,6,7-tetrahydro-1H-cyclopenta[b]pyridin-4-one-3-carboxamide; mp=294–295° C. (Compound 28).

(aa) N-(4-methyl-2-thiazolyl)-4,5,6,7-tetrahydro-1H-cyclopenta[b]pyridin-4-one-3-carboxamide; mp=304–305° C. (Compound 29).

(bb) N-(3-fluorophenyl)-4,5,6,7-tetrahydro-1H-cyclopenta[b]pyridin-4-one-3-carboxamide; mp=340° (dec.) (Compound 30).

(cc) N-(2-fluorophenyl)-4,5,6,7-tetrahydro-1H-cyclopenta[b]pyridin-4-one-3-carboxamide; mp=330° (dec.) (Compound 31).

(dd) N-(2,4-difluorophenyl)-4,5,6,7-tetrahydro-1H-cyclopenta[b]pyridin-4-one-3-carboxamide; mp=328° (dec.) (Compound 32).

(ee) N-(2,6-difluorophenyl)-4,5,6,7-tetrahydro-1H-cyclopenta[b]pyridin-4-one-3-carboxamide; mp=297° (dec.) (Compound 33).

(ff) N-(benzyl)-4,5,6,7-tetrahydro-1H-cyclopenta[b]pyridin-4-one-3-carboxamide; mp=149–150° C. (Compound 34).

(gg) N-(3-methoxybenzyl)-4,5,6,7-tetrahydro-1H-cyclopenta[b]pyridin-4-one-3-carboxamide; mp=204–205° C. (Compound 35).

(hh) N-(2-methoxybenzyl)-4,5,6,7-tetrahydro-1H-cyclopenta[b]pyridin-4-one-3-carboxamide; mp=243–244° C. (Compound 36).

(ii) N-(2,6-difluorobenzyl)-4,5,6,7-tetrahydro-1H-cyclopenta[b]pyridin-4-one-3-carboxamide; mp=294–295° C. (Compound 37).

(jj) N-(2-thienyl)-4,5,6,7-tetrahydro-1H-cyclopenta[b]pyridin-4-one-3-carboxamide; mp=210° (dec.) (Compound 38).

(kk) N-butyl-4,5,6,7,8,9-hexahydro-1H-cyclohepta[b]pyridin-4-one-3-carboxamide; mp=138–143° C. (Compound 39).

(ll) N-(2-thiazolyl)-4,5,6,7,8,9-hexahydro-1H-cyclohepta[b]pyridin-4-one-3-carboxamide; mp=301° C. (dec.) (Compound 40).

(mm) N-(4-methoxyphenyl)-4,5,6,7,8,9-hexahydro-1H-cyclohepta[b]pyridin-4-one-3-carboxamide; mp=240–242° C. (Compound 41).

(nn) N-(benzyl)-4,5,6,7,8,9-hexahydro-1H-cyclohepta[b]pyridin-4-one-3-carboxamide; mp=224–226° C. (Compound 42).

(oo) N-(4-methoxybenzyl)-4,5,6,7,8,9-hexahydro-1H-cyclohepta[b]pyridin-4-one-3-carboxamide; mp=203–205° C. (Compound 43).

(pp) N-(4-fluorobenzyl)-4,5,6,7,8,9-hexahydro-1H-cyclohepta[b]pyridin-4-one-3-carboxamide; mp=219–222° C. (Compound 44).

(qq) N-(3-fluorobenzyl)-1,4,5,6,7,8-hexahydroquinolin-4-one-3-carboxamide; mp=267–270° C. (Compound 45).

(rr) N-(4-fluorobenzyl)-1,4,5,6,7,8-hexahydroquinolin-4-one-3-carboxamide; mp=278–280° C. (Compound 46).

(ss) N-(3-chlorobenzyl)-1,4,5,6,7,8-hexahydroquinolin-4-one-3-carboxamide; mp=247–249° C. (Compound 47).

(tt) N-(4-chlorobenzyl)-1,4,5,6,7,8-hexahydroquinolin-4-one-3-carboxamide; mp=283–285° C. (Compound 48).

(uu) N-(2-fluoro-4-methoxybenzyl)-1,4,5,6,7,8-hexahydroquinolin-4-one-3-carboxamide; mp=257–259° C. (Compound 49).

(vv) N-(4-ethoxybenzyl)-1,4,5,6,7,8-hexahydroquinolin-4-one-3-carboxamide; mp=241–243° C. (Compound 50).

(ww) N-(4-methylbenzyl)-1,4,5,6,7,8-hexahydroquinolin-4-one-3-carboxamide; mp=270–273° C. (Compound 51).

(xx) N-(3-methylbenzyl)-1,4,5,6,7,8-hexahydroquinolin-4-one-3-carboxamide; mp=242–245° C. (Compound 52).

(yy) N-(2-fluoro-4-ethoxybenzyl)-1,4,5,6,7,8-hexahydroquinolin-4-one-3-carboxamide; mp=178–181° C. (Compound 53).

(zz) N-(2-fluoro-4-isopropoxybenzyl)-1,4,5,6,7,8-hexahydroquinolin-4-one-3-carboxamide; mp=197–200° C. (Compound 54).

(aaa) N-(2-fluoro-4-propyl)-1,4,5,6,7,8-hexahydroquinolin-4-one-3-carboxamide; mp=189–191° C. (Compound 55).

(bbb) N-(2-thienylmethyl)-1,4,5,6,7,8-hexahydroquinolin-4-one-3-carboxamide; mp=245–248° C. (Compound 56).

(ccc) N-(4-methoxyphenyl)-4,5,6,7-tetrahydro-1H-cyclopenta[b]pyridin-4-one-3-carboxamide; mp=330–332° C. (Compound 57).

(ddd) N-(3-methoxyphenyl)-4,5,6,7-tetrahydro-1H-cyclopenta[b]pyridin-4-one-3-carboxamide; mp=320° C. (dec.) (Compound 58).

(eee) N-(4-(2-hydroxyethoxy)phenyl)-4,5,6,7-tetrahydro-1H-cyclopenta[b]pyridin-4-one-3-carboxamide; mp=220–222° C. (Compound 59).

(fff) N-((4-(dimethylamino)phenyl)methyl)-4,5,6,7-tetrahydro-1H-cyclopenta[b]pyridin-4-one-4–3-carboxamide; mp=269–270° C. (Compound 60).

(ggg) N-(2-fluoro-4-methoxybenzyl)-4,5,6,7-tetrahydro-1H-cyclopenta[b]pyridin-4-one-4–3-carboxamide; mp=238–240° C. (Compound 61).

(hhh) N-(4-ethoxybenzyl)-4,5,6,7-tetrahydro-1H-cyclopenta[b]pyridin-4-one-4–3-carboxamide; mp=243–245° C. (Compound 62).

(iii) N-(2-fluoro-4-ethoxybenzyl)-4,5,6,7-tetrahydro-1H-cyclopenta[b]pyridin-4-one-3-carboxamide; mp=217–219° C (Compound 63).

(jjj) N-(2-fluoro-4-isopropoxybenzyl)-4,5,6,7-tetrahydro-1H-cyclopenta[b]pyridin-4-one-3-carboxamide; mp=214° C. (dec.) (Compound 64).

(kkk) N-(2-fluoro-4-propoxybenzyl)-4,5,6,7-tetrahydro-1H-cyclopenta[b]pyridin-4-one-3-carboxamide; mp=209–211° C. (Compound 65).

(lll) N-(2-fluorobenzyl)-4,5,6,7-tetrahydro-1H-cyclopenta[b]pyridin-4-one-3-carboxamide; mp=259–261° C. (Compound 66).

EXAMPLE 4

The pharmaceutical utility of compounds of this invention are indicated by the following assay for GABAa receptor activity.

Assays are carried out as described in Thomas and Tallman (J. Bio. Chem. 156: 9838–9842, J. Neurosci. 3: 433–440, 1983). Rat cortical tissue is dissected and homogenized in 25 volumes (w/v) of 0.05 M Tris HCl buffer (pH 7.4 at 4° C.). The tissue homogenate is centrifuged in the cold (40) at 20,000×g for 20'. The supernatant is decanted and the pellet is rehomogenized in the same volume of buffer and again centrifuged at 20,000×g. The supernatant is decanted and the pellet is frozen at −20° C. overnight. The pellet is then thawed and rehomogenized in 25 volume (original wt/vol) of buffer and the procedure is carried out twice. The pellet is finally resuspended in 50 volumes (w/vol of 0.05 M Tris HCl buffer (pH 7.4 at 40° C.).

Incubations contain 100 ml of tissue homogenate, 100 ml of radioligand 0.5 nM ($^3$H-RO15-1788 [$^3$H-Flumazenil] specific activity 80 Ci/mmol), drug or blocker and buffer to a total volume of 500 ml. Incubations are carried for 30 min at 4° C. then are rapidly filtered through GFB filters to separate free and bound ligand. Filters are washed twice with fresh 0.05 M Tris HCl buffer (pH 7.4 at 4° C.) and counted in a liquid scintillation counter. 1.0 mM diazepam is added to some tubes to determine nonspecific binding. Data are collected in triplicate determinations, averaged and % inhibition of total specific binding is calculated. Total Specific Binding=Total−Nonspecific. In some cases, the amounts of unlabeled drugs is varied and total displacement curves of binding are carried out. Data are converted to a form for the calculation of $IC_{50}$ and Hill Coefficient (nH). In the described assays compounds have Ki's of less than 1 µM.

EXAMPLE 5

In addition, the following assay may be used to determine if the compounds of the invention are agonists, antagonists, or inverse agonists, and, therefore, their specific pharmaceutical utility. The following assay can be employed to determine specific GABAa receptor activity.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Xenopus Laevis oocytes are enzymatically isolated and injected with non-polyadenylated cRNA mixed in a ratio of 4:1:4 for human derived α, β, and γ subunits, respectively. For each subunit combination, sufficient message is injected to result in current amplitudes of >10 nA when 1 μM GABA is applied.

Electrophysiological recordings are carried out using the two electrode voltage-clamp technique at a membrane holding potential of −70 mV.

Compounds are evaluated against a GABA concentration that evokes <10% of the maximal evokable GABA current. Each oocyte is exposed to increasing concentrations of compound in order to evaluate a concentration/effect relationship. Compound efficacy is expressed as a percent-change in current amplitude: $100*((Ic/I)-1)$, where Ic is the GABA evoked current amplitude observed in the presence of compound and I is the GABA evoked current amplitude observed in the absence of compound.

Specificity of a compound for the Ro15-788 site is determined following completion of the concentration/effect curve. After washing the oocyte sufficiently to remove previously applied compound, the oocyte is exposed to GABA+1 μM Ro15-1788, followed by exposure to GABA+1 μM Ro15-1788+compound. Percent change due to addition of compound is calculated as described above. Any percent change observed in the presence of Ro15-1788 is subtracted from the percent changes in current amplitude observed in the absence of 1 μM Ro15-1788. These net values are used for the calculation of average efficacy and $EC_{50}$ values.

To evaluate average efficacy and $EC_{50}$ values, the concentration/effect data are averaged across cells and fit to the logistic equation. Average values are reported as mean ±standard error.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

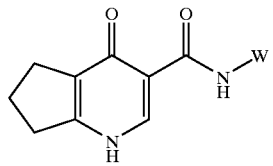

or a pharmaceutically acceptable non-toxic salt thereof wherein:

$R_3$ and $R_4$ are the same or different and represent hydrogen,

W is $C_1$–$C_6$ alkyl, fluorophenyl, difluorophenyl, benzyl, methoxybenzyl, difluorobenzyl, methoxyphenyl, fluorobenzyl, (fluoro)(methoxy)benzyl, (fluoro)(ethoxy)benzyl, (fluoro)(isopropoxy)benzyl, (fluoro) (propoxy)benzyl, (2-hydroxyethoxy)phenyl, (dimethylamino)benzyl, or ethoxybenzyl.

2. A compound or salt according to claim 1, wherein W is butyl.

3. A compound or salt according to claim 1, wherein W is 2-, 3-, or 4-fluorophenyl, 2,4- or 2,6-difluorophenyl, benzyl, 2- or 3-methoxybenzyl, 2,6-difluorobenzyl, 3- or 4-methoxyphenyl, 2-fluorobenzyl, 2-fluoro-4-methoxybenzyl, 2-fluoro-4-ethoxybenzyl, 2-fluoro-4-isopropoxybenzyl, 2-fluoro-4-propoxybenzyl, 4-(2-hydroxyethoxy)phenyl, 4-(dimethylamino)benzyl, 4-ethoxybenzyl.

4. A compound of the formula

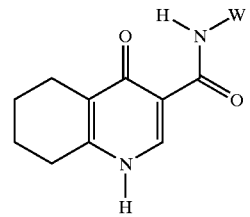

or a pharmaceutically acceptable non-toxic salt thereof wherein:

W is phenyl or benzyl where the phenyl portion of each is hydroxyphenyl, difluorophenyl, fluorophenyl, chlorophenyl, (fluoro)(methoxy)phenyl, (fluoro) (ethoxy)phenyl, (fluoro)(isopropoxy)phenyl, methoxyphenyl, ethoxyphenyl, methylphenyl, piperonyl, or (fluoro)(propyl)phenyl.

5. A compound or salt according to claim 4, wherein W is phenyl or benzyl where the phenyl portion of each is 2-hydroxyphenyl, 3-hydroxyphenyl, 2-fluorophenyl, 3-fluorophenyl, 4-fluorophenyl, 3-chlorophenyl, 2,6-difluorophenyl, 4-chlorophenyl, 2-fluoro-4-methoxyphenyl, 2-fluoro-4-ethoxyphenyl, 2-fluoro-4-isopropoxyphenyl, 2-methoxyphenyl, 3-methoxyphenyl, 4-methoxyphenyl, 4-ethoxyphenyl, 3-methylphenyl, 4-methylphenyl, piperonyl, or 2-fluoro-4-propylphenyl.

6. A compound of the formula:

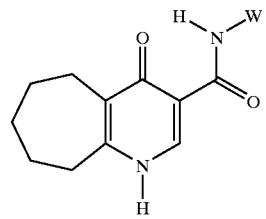

or a pharmaceutically acceptable non-toxic salt thereof wherein:

W is $C_1$–$C_6$ alkyl, thiazolyl, or phenyl or benzyl where the phenyl portion of each is optionally substituted with one or two groups independently selected from halogen, trifluoromethyl, cyano, hydroxy, lower alkyl, lower alkoxy, amino, mono or dialkylamino where each alkyl portion is lower alkyl, methylaminoalkyl where each alkyl portion is lower alkyl, $NR_1COR_2$, $COR_2$, $CONR_1R_2$ or $CO_2R_2$ where $R_1$ and $R_2$ are the same or different and represent hydrogen or lower alkyl.

7. A compound according to claim 1 which is selected from

N-(3-fluorophenyl)-4,5,6,7-tetrahydro-1H-cyclopenta[b] pyridin-4-one-3-carboxamide;

N-(2-fluorophenyl)-4,5,6,7-tetrahydro-1H-cyclopenta[b]pyridin-4-one-3-carboxamide;

N-(2,4-difluorophenyl)-4,5,6,7-tetrahydro-1H-cyclopenta[b]pyridin-4-one-3-carboxamide; and N-(2,6-difluorophenyl)-4,5,6,7-tetrahydro-1H-cyclopenta[b]pyridin-4-one-3-carboxamide N-(benzyl)-4,5,6,7-tetrahydro-1H-cyclopenta[b]pyridin-4-one-3-carboxamide;

N-(3-methoxybenzyl)-4,5,6,7-tetrahydro-1H-cyclopenta[b]pyridin-4-one-3-carboxamide;

N-(2-methoxybenzyl)-4,5,6,7-tetrahydro-1H-cyclopenta[b]pyridin-4-one-3-carboxamide;

N-(4-methoxybenzyl)-4,5,6,7-tetrahydro-1H-cyclopenta[b]pyridin-4-one-3-carboxamide; and N-(2,6-difluorobenzyl)-4,5,6,7-tetrahydro-1H-cyclopenta[b]pyridin-4-one-3-carboxamide.

8. A compound according to claim 4 which is selected from

N-(2-fluorobenzyl)-1,4,5,6,7,8-hexahydroquinolin-4-one-3-carboxamide;

N-(2-fluoro-4-methoxyphenyl)-1,4,5,6,7,8-hexahydroquinolin-4-one-3-carboxamide;

N-(3-fluorobenzyl)-1,4,5,6,7,8-hexahydroquinolin-4-one-3-carboxamide;

N-(4-fluorobenzyl)-1,4,5,6,7,8-hexahydroquinolin-4-one-3-carboxamide;

N-(3-chlorobenzyl)-1,4,5,6,7,8-hexahydroquinolin-4-one-3-carboxamide;

N-(4-chlorobenzyl)-1,4,5,6,7,8-hexahydroquinolin-4-one-3-carboxamide;

N-(2-fluorophenyl)-1,4,5,6,7,8-hexahydroquinolin-4-one-3-carboxamide;

N-(4-methoxybenzyl)-1,4,5,6,7,8-hexahydroquinolin-4-one-3-carboxamide;

N-(piperonyl)-1,4,5,6,7,8-hexahydroquinolin-4-one-3-carboxamide;

N-(3-fluorophenyl)-1,4,5,6,7,8-hexahydroquinolin-4-one-3-carboxamide;

N-(4-methoxyphenyl)-1,4,5,6,7,8-hexahydroquinolin-4-one-3-carboxamide;

N-(4-fluorophenyl)-1,4,5,6,7,8-hexahydroquinolin-4-one-3-carboxamide; and

N-(2-fluoro-4-methoxybenzyl)-1,4,5,6,7,8-hexahydroquinolin-4-one-3-carboxamide.

9. A compound according to claim 6 which is selected from

N-butyl-4,5,6,7,8,9-hexahydro-1H-cyclohepta[b]pyridin-4-one-3-carboxamide;

N-(4-methoxyphenyl)-4,5,6,7,8,9-hexahydro-1H-cyclohepta[b]pyridin-4-one-3-carboxamide;

N-(benzyl)-4,5,6,7,8,9-hexahydro-1H-cyclohepta[b]pyridin-4-one-3-carboxamide;

N-(4-methoxybenzyl)-4,5,6,7,8,9-hexahydro-1H-cyclohepta[b]pyridin-4-one-3-carboxamide; and N-(4-fluorobenzyl)-4,5,6,7,8,9-hexahydro-1H-cyclohepta[b]pyridin-4-one-3-carboxamide.

10. A compound according to claim 6 which is selected from

N-butyl-4,5,6,7,8,9-hexahydro-1H-cyclohepta[b]pyridin-4-one-3-carboxamide; and

N-(4-methoxyphenyl)-4,5,6,7,8,9-hexahydro-1H-cyclohepta[b]pyridin-4-one-3-carboxamide;

N-(benzyl)-4,5,6,7,8,9-hexahydro-1H-cyclohepta[b]pyridin-4-one-3-carboxamide;

N-(4-methoxybenzyl)-4,5,6,7,8,9-hexahydro-1H-cyclohepta[b]pyridin-4-one-3-carboxamide; and N-(4-fluorobenzyl)-4,5,6,7,8,9-hexahydro-1H-cyclohepta[b]pyridin-4-one-3-carboxamide.

11. A compound according to claim 4 which is selected from

N-(4-ethoxybenzyl)-1,4,5,6,7,8-hexahydroquinolin-4-one-3-carboxamide;

N-(4-methylbenzyl)-1,4,5,6,7,8-hexahydroquinolin-4-one-3-carboxamide;

N-(3-methylbenzyl)-1,4,5,6,7,8-hexahydroquinolin-4-one-3-carboxamide;

N-(2-fluoro-4-ethoxybenzyl)-1,4,5,6,7,8-hexahydroquinolin-4-one-3-carboxamide;

N-(2-fluoro-4-isopropoxybenzyl)-1,4,5,6,7,8-hexahydroquinolin-4-one-3-carboxamide;

N-(2-fluoro-4-propyl)-1,4,5,6,7,8-hexahydroquinolin-4-one-3-carboxamide;

N-(3-methoxyphenyl)-1,4,5,6,7,8-hexahydroquinolin-4-one-3-carboxamide;

N-(3-hydroxybenzyl)-1,4,5,6,7,8-hexahydroquinolin-4-one-3-carboxamide;

N-(2-chlorophenyl)-1,4,5,6,7,8-hexahydroquinolin-4-one-3-carboxamide;

N-(2,6-difluorophenyl)-1,4,5,6,7,8-hexahydroquinolin-4-one-3-carboxamide;

N-(2-methoxybenzyl)-1,4,5,6,7,8-hexahydroquinolin-4-one-3-carboxamide; and

N-(3-methoxybenzyl)-1,4,5,6,7,8-hexahydroquinolin-4-one-3-carboxamide.

12. A compound according to claim 1 which is selected from

N-(3-methoxyphenyl)-4,5,6,7-tetrahydro-1H-cyclopenta[b]pyridin-4-one-3-carboxamide;

N-(4-(2-hydroxyethoxy)phenyl)-4,5,6,7-tetrahydro-1H-cyclopenta[b]pyridin-4-one-3-carboxamide;

N-((4-(dimethylamino)phenyl)methyl)-4,5,6,7-tetrahydro-1H-cyclopenta[b]pyridin-4-one-3-carboxamide;

N-(2-fluoro-4-methoxybenzyl)-4,5,6,7-tetrahydro-1H-cyclopenta[b]pyridin-4-one-3-carboxamide;

N-(4-ethoxybenzyl)-4,5,6,7-tetrahydro-1H-cyclopenta[b]pyridin-4-one-3-carboxamide;

N-(2-fluoro-4-ethoxybenzyl)-4,5,6,7-tetrahydro-1H-cyclopenta[b]pyridin-4-one-3-carboxamide;

N-(2-fluoro-4-isopropoxybenzyl)-4,5,6,7-tetrahydro-1H-cyclopenta[b]pyridin-4-one-3-carboxamide;

N-(2-fluoro-4-propoxybenzyl)-4,5,6,7-tetrahydro-1H-cyclopenta[b]pyridin-4-one-3-carboxamide;

N-(2-fluorobenzyl)-4,5,6,7-tetrahydro-1H-cyclopenta[b]pyridin-4-one-3-carboxamide.

13. A pharmaceutical composition comprising a compound of formula A together with a pharmaceutically acceptable carrier, where formula A is

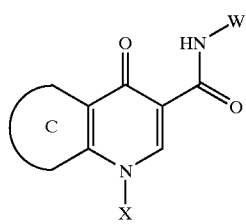

or a pharmaceutically acceptable non-toxic salt thereof wherein:

the C ring represents a carbocyclic group having from 5–7 members, where any member of the carbocyclic group is optionally substituted with lower alkyl, $C_1$–$C_6$ alkoxy, hydroxy, halogen, amino, mono- or di($C_1$–$C_6$) alkylamino, or trifluoromethyl;

X is hydrogen, hydroxy, or lower alkyl; and

W is lower alkyl optionally substituted with halogen, hydroxy, lower alkoxy, amino, mono or dialkylamino where each alkyl portion is lower alkyl; or W is heteroaryl, where each heteroaryl is optionally substituted with one or two groups independently selected from halogen, trifluoromethyl, cyano, hydroxy, lower alkyl, lower alkoxy, amino, mono- or dialkylamino where each alkyl portion is lower alkyl, methylaminoalkyl where each alkyl portion is lower alkyl, or $NR_1COR_2$, $COR_2$, $CONR_1R_2$ or $CO_2R_2$ where $R_1$ and $R_2$ are the same or different and represent hydrogen or lower alkyl.

14. A pharmaceutical composition comprising a compound of claim 1 and at least one pharmaceutically acceptable carrier or excipient.

15. A pharmaceutical composition comprising a compound of claim 4 and at least one pharmaceutically acceptable carrier or excipient.

16. A pharmaceutical composition comprising a compound of claim 6 and at least one pharmaceutically acceptable carrier or excipient.

17. A method for treating anxiety, depression or a sleep disorder in a patient comprising administering to the patient in need thereof a therapeutically effective amount of a compound of claim 1 or a pharmaceutically acceptable non-toxic salt thereof.

18. A method for treating anxiety, depression or a sleep disorder in a patient comprising administering to the patient in need thereof a therapeutically effective amount of a compound of claim 4 or a pharmaceutically acceptable non-toxic salt thereof.

19. A method for treating anxiety, depression or a sleep disorder in a patient comprising administering to the patient in need thereof a therapeutically effective amount of a compound of claim 6 or a pharmaceutically acceptable non-toxic salt thereof.

* * * * *